United States Patent
Torvinen et al.

(10) Patent No.: US 11,678,816 B2
(45) Date of Patent: Jun. 20, 2023

(54) WIRELESS DATA COMMUNICATION AND POWER TRANSMISSION ATHLETIC APPAREL MODULE

(71) Applicant: adidas AG, Herzogenaurach (DE)

(72) Inventors: Vesa-Pekka Torvinen, Herzogenaurach (DE); Michael Welker, Herzogenaurach (DE); Marc Norridge, Herzogenaurach (DE); Jon Werner, Portland, OR (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 17/509,807

(22) Filed: Oct. 25, 2021

(65) Prior Publication Data

US 2022/0046125 A1 Feb. 10, 2022

Related U.S. Application Data

(63) Continuation of application No. 16/985,938, filed on Aug. 5, 2020, now Pat. No. 11,159,667, which is a
(Continued)

(51) Int. Cl.
*H04M 1/72409* (2021.01)
*A61B 5/00* (2006.01)
(Continued)

(52) U.S. Cl.
CPC ....... *H04M 1/72409* (2021.01); *A61B 5/0024* (2013.01); *A61B 5/02* (2013.01);
(Continued)

(58) Field of Classification Search
CPC ......... H04M 1/72409; H04M 1/72412; H04M 1/724094; A61B 5/0024; A61B 5/02;
(Continued)

(56) References Cited

U.S. PATENT DOCUMENTS 6,725,061 B1 * 4/2004 Hutchison, IV .... H04M 1/6083
455/420
8,253,586 B1 * 8/2012 Matak ..................... G06F 17/00
340/870.07
(Continued)

FOREIGN PATENT DOCUMENTS

CA 2960003 A1 3/2016
JP 2015-150375 A 8/2015
(Continued)

OTHER PUBLICATIONS

Michael deAgonia, How does Apple Pay Work on the Apple Watch, Mar. 13, 2015, Computerworld 11 pages (Year: 2015).

*Primary Examiner* — Lewis G West
(74) *Attorney, Agent, or Firm* — Sterne, Kessler, Goldstein & Fox P.L.L.C.

(57) ABSTRACT

The present disclosure describes devices, systems, and methods that can be used to collect sensor data from, for instance, a sensor device that has been embedded in an article of apparel. The sensor device can be used, for instance, to monitor the athletic activity of an individual wearing the apparel into which the electronic device has been embedded. Embodiments of the sensor device include a memory, a wireless interface, and one or more processor. With these elements, the sensor device may receive instructions indicating what sensor data to collect, collect the sensor data, store the sensor data, and transmit the stored sensor data to the remote device upon completion of the activity.

20 Claims, 13 Drawing Sheets

Related U.S. Application Data continuation of application No. 16/356,226, filed on Mar. 18, 2019, now Pat. No. 10,742,790, which is a continuation of application No. 15/375,748, filed on Dec. 12, 2016, now Pat. No. 10,237,388.

(51) Int. Cl.

| | | |
|---|---|---|
| *A61B 5/02* | (2006.01) | |
| *A61B 5/103* | (2006.01) | |
| *H04W 4/70* | (2018.01) | |
| *H04W 76/27* | (2018.01) | |
| *H04B 1/3827* | (2015.01) | |

(52) U.S. Cl.
CPC .............. *A61B 5/103* (2013.01); *A61B 5/681* (2013.01); *A61B 5/6802* (2013.01); *A61B 5/6803* (2013.01); *A61B 5/6804* (2013.01); *H04B 1/385* (2013.01); *H04W 4/70* (2018.02); *H04W 76/27* (2018.02); *A61B 2503/10* (2013.01); *A61B 2560/0214* (2013.01)

(58) Field of Classification Search
CPC ..... A61B 5/103; A61B 5/6802; A61B 5/6803; A61B 5/6804; A61B 5/681; A61B 2503/10; A61B 2560/0214; H04B 1/385; H04W 4/70; H04W 76/27; H04W 4/00; A41D 13/0015
See application file for complete search history.

(56) References Cited

U.S. PATENT DOCUMENTS

| | | | |
|---|---|---|---|
| 8,745,247 B1 * | 6/2014 | Park | G08C 17/02 709/200 |
| 9,100,493 B1 * | 8/2015 | Zhou | H04M 1/0272 |
| 9,392,523 B1 * | 7/2016 | Arestani | H04L 65/1069 |
| 9,392,941 B2 | 7/2016 | Powch et al. | |
| 9,492,922 B1 | 11/2016 | Johnson et al. | |
| 9,595,181 B2 * | 3/2017 | Katingari | G08B 25/10 |
| 9,658,066 B2 * | 5/2017 | Yuen | A61B 5/1118 |
| 9,712,629 B2 * | 7/2017 | Molettiere | H04L 43/0876 |
| 10,026,094 B2 * | 7/2018 | Van Os | G06Q 20/36 |
| 10,237,388 B2 | 3/2019 | Torvinen et al. | |
| 10,332,079 B2 * | 6/2019 | Van Os | G06Q 20/08 |
| 10,413,816 B2 * | 9/2019 | Moir | A63F 13/25 |
| 10,742,790 B2 | 8/2020 | Torvinen et al. | |
| 10,983,945 B2 * | 4/2021 | Molettiere | G16H 10/60 |
| 11,159,667 B2 | 10/2021 | Torvinen et al. | |
| 2002/0065712 A1 * | 5/2002 | Kawan | G06Q 30/0236 705/41 |
| 2006/0000900 A1 * | 1/2006 | Fernandes | G06Q 20/24 235/380 |
| 2010/0106220 A1 | 4/2010 | Ecker et al. | |
| 2011/0248846 A1 | 10/2011 | Belov et al. | |
| 2012/0015778 A1 * | 1/2012 | Lee | A63B 71/0686 482/8 |
| 2012/0203491 A1 | 8/2012 | Sun et al. | |
| 2012/0239173 A1 * | 9/2012 | Laikari | G16H 40/67 700/91 |
| 2013/0166048 A1 * | 6/2013 | Werner | G06Q 10/10 700/91 |
| 2014/0241555 A1 * | 8/2014 | Terlizzi | H02J 50/10 320/108 |
| 2015/0116127 A1 | 4/2015 | Lynch et al. | |
| 2015/0177063 A1 | 6/2015 | Lian et al. | |
| 2016/0133085 A1 * | 5/2016 | Eagon | G07F 17/248 705/13 |
| 2016/0248266 A1 | 8/2016 | Ferrese et al. | |
| 2016/0323825 A1 | 11/2016 | Yamaji et al. | |
| 2016/0325179 A1 * | 11/2016 | Moir | A63F 13/25 |
| 2016/0354033 A1 | 12/2016 | Ouchi et al. | |
| 2016/0354042 A1 * | 12/2016 | Shim | A61B 5/024 |
| 2016/0358134 A1 * | 12/2016 | Van Os | G06Q 20/3278 |
| 2017/0013562 A1 * | 1/2017 | Lim | H04M 1/725 |
| 2017/0026800 A1 * | 1/2017 | Kim | H04W 4/80 |
| 2018/0070840 A1 | 3/2018 | Cronin et al. | |
| 2018/0167499 A1 | 6/2018 | Torvinen et al. | |
| 2018/0240097 A1 * | 8/2018 | Chauvin | G06Q 20/3227 |
| 2018/0256078 A1 * | 9/2018 | Vaterlaus | G16H 20/30 |
| 2019/0215394 A1 | 7/2019 | Torvinen et al. | |
| 2021/0084140 A1 | 3/2021 | Torvinen et al. | |
| 2022/0103675 A1 * | 3/2022 | Hulbert | G06Q 20/3278 |

FOREIGN PATENT DOCUMENTS

| | | |
|---|---|---|
| JP | 2016-127942 A | 7/2016 |
| JP | 2016-208462 A | 12/2016 |
| JP | 2018-513716 A | 5/2018 |
| JP | 2018-126495 A | 8/2018 |
| WO | WO 2016/035884 A1 | 3/2016 |
| WO | WO 2016/094433 A1 | 6/2016 |
| WO | WO 2016/146652 A1 | 9/2016 |
| WO | WO 2016/196304 A1 | 12/2016 |

* cited by examiner

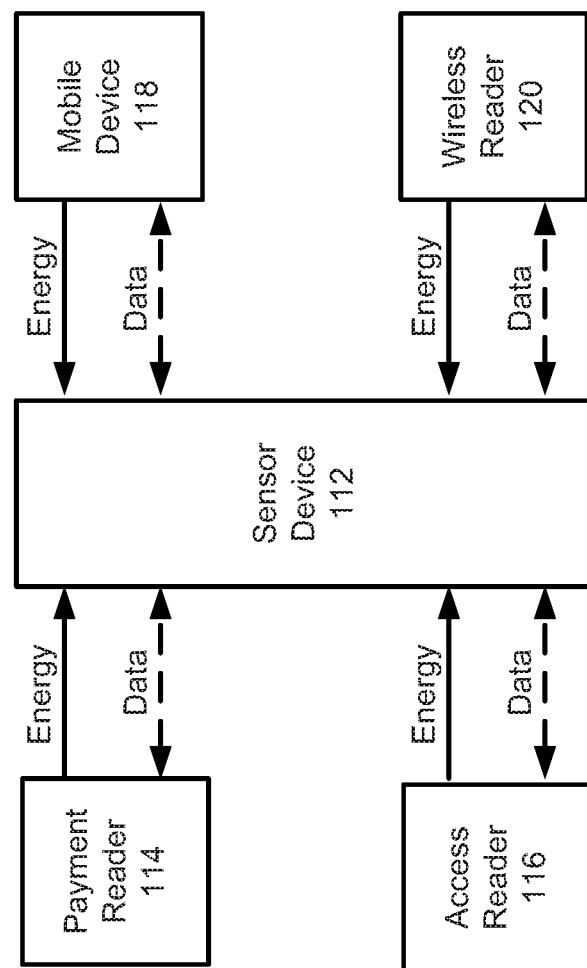

WIRELESS DATA COMMUNICATION AND POWER TRANSMISSION ATHLETIC APPAREL MODULE

CROSS-REFERENCE TO RELATED APPLICATIONS

This application claims priority as a continuation of U.S. patent application Ser. No. 16/985,938, filed on Aug. 5, 2020, which is a continuation of U.S. patent application Ser. No. 16/356,226, filed on Mar. 18, 2019, now U.S. Pat. No. 10,742,790, which is a continuation of U.S. patent application Ser. No. 15/375,748, filed on Dec. 12, 2016, now U.S. Pat. No. 10,237,388, each of which are incorporated by reference herein in their entireties.

FIELD OF THE INVENTION

Embodiments of the present invention generally relate to methods and systems that collect and read sensor data using sensors that are embedded in an article of apparel. More particularly, embodiments of the present invention relate to methods and systems for collecting sensor data for an individual during an athletic activity.

BACKGROUND OF THE INVENTION

Athletic activity can take many forms—some individuals prefer to engage in team athletic activities such as, for example, soccer or basketball, while other individuals prefer to engage in individual athletic activities such as, for example, running or skiing. Regardless of whether the activity is a team or individual activity, it is becoming more and more common for individuals to actively track their performance.

To that end, athletic monitoring devices can be employed to record information about an individual's performance during an athletic activity using sensors, and in some cases providing feedback about the individual's performance. Some portable athletic monitoring devices employ sensors attached to a piece of athletic equipment. Such sensors may be capable of measuring various parameters associated with the individual's physical activity, such as motion parameters.

BRIEF SUMMARY OF THE INVENTION

Embodiments of the present disclosure relate to devices, systems, and methods that can be used to collect sensor data from, for instance, a sensor device that has been embedded in an article of apparel. For instance, according to an embodiment, an electronic device that is embedded in an article of apparel is provided. In various embodiments, the electronic device may be either removable or permanently embedded, attached, or adhered to the article of apparel. The electronic device can be used, for instance, to monitor the athletic activity of an individual wearing the apparel into which the electronic device has been embedded. According to embodiments, the electronic device may include a memory, a wireless interface, and one or more processors communicatively coupled to the wireless interface and the memory. The wireless interface may be further configured to receive power from and transmit data to a remote electronic device. Furthermore, the one or more processors may be configured to receive a first signal from the remote electronic device via the wireless interface. Additionally, the one or more processors may be configured to store sensor data recorded by one or more sensors that are associated with the electronic device in the memory. Upon receiving a second signal from the remote electronic device via the wireless interface, the one or more processors may also be configured to transmit the stored data to the remote electronic device via the wireless interface. In some, but not all embodiments, transmitting the stored data to the remote electronic device may be automatic in response to receiving the second signal.

In some embodiments, the one or more processors may be further configured to set a state of the electronic device. For instance, in a first state, the electronic device may be configured to power off one or more sensors associated with the electronic device and power on the wireless interface. Conversely, in a second state, the one or more processors may be configured to power on one or more sensors and power off the wireless interface.

In some embodiments, the first signal from the remote device may specify particular sensor data to be collected by the sensors associated with the electronic device. Accordingly, in some embodiments, the one or more processors may be further configured to modify the type of sensor data that is recorded in based on the information contained in the first signal form the remote device. The first signal may also specify a duration for which one or more sensors should record sensor data according to some embodiments. In some embodiments, the one or more processors may be further configured to place the electronic device into a sleep state after the specified duration has elapsed.

According to some embodiments, a method of collecting sensor data from an electronic device embedded in apparel worn by an individual engaged in an athletic activity is provided. According to embodiments, the method may include receiving a first signal from a remote electronic device via a wireless interface. Sensor data recorded by one or more sensors associated with the electronic device may then be stored in memory. Additionally, upon receiving a second signal from the remote electronic device via the wireless interface, the stored data may be transmitted to the remote electronic device via the wireless interface.

Embodiments of the disclosure also include electronic devices for monitoring sensor data generated by a sensor device embedded in an article of apparel. As noted above, the sensor device may either be removable or permanently embedded, adhered, or attached to the article of apparel. According to embodiments, the electronic device may include a wireless interface configured to transmit and receive power to and from a sensor device. Additionally, the electronic device may include one or more processors communicatively coupled to the wireless interface. The one or more processors may be configured to transmit a data signal to the sensor device via the wireless interface. The data signal may specify sensor data to be collected by the sensor device. According to some embodiments, the one or more processors may be configured to transmit a power signal to the sensor device via the wireless interface.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

FIG. 1B is a functional block diagram depicting a sensor device in conjunction with several readers according to various embodiments.

DETAILED DESCRIPTION OF THE INVENTION

Figure 1A:
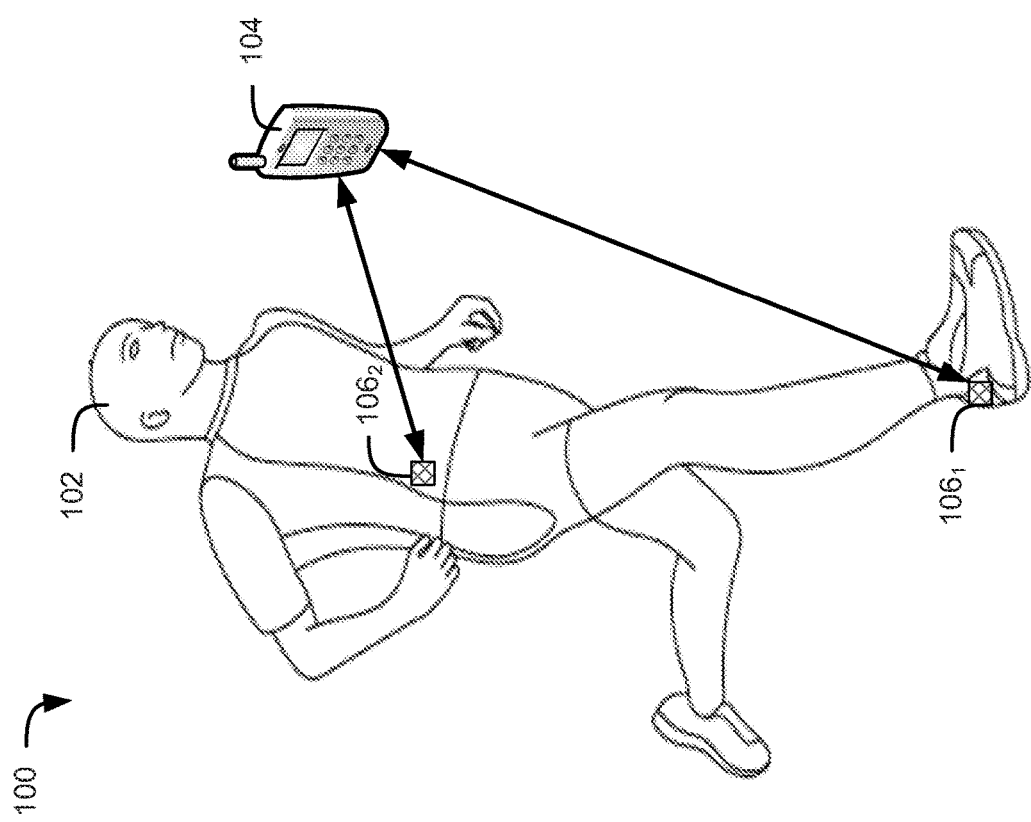
FIG. 1A is an illustration of a monitoring system using one or more sensor devices embedded in articles of apparel according to various embodiments.

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The present invention generally relates to methods and systems that collect, store, and communicate sensor data from a sensing device such as a sensing device embedded in an article of apparel. More particularly, embodiments of the present invention relate to methods and systems for collecting sensor data from a sensor device using a remote device to wirelessly power and communicate with the sensor device. Embodiments of the present invention may also relate to methods and systems for monitoring the output of a sensor device that has been embedded in an item such as an article of apparel and that may provide data indicative of athletic performance. An individual engaged in an athletic activity (or another interested person such as a coach, teammate, or spectator) may desire to obtain information about activities performed by the wearer of the article of apparel during the course of, for example, an athletic activity.

In some embodiments, if an individual wearing an article of apparel with an embedded sensor device participates in an activity, it may be desirable to, for example, determine various characteristics (e.g., heart rate, breathing, steps, speed, distance, location, acceleration, temperature, moisture, ambient light, sound, altitude, pressure, or pace, etc.) for use in training.

In an embodiment, the movement of a plurality of pieces of athletic equipment used by a plurality of individuals engaged in an athletic activity (e.g., teammates or opponents in a team sport) may be monitored. In some embodiments, real-time monitoring and/or feedback may be provided, while in other embodiments post-activity feedback may be provided. In some embodiments, feedback may be provided by an athletic equipment motion monitoring system portable electronic device software application. Suitable software applications may include, for example, those disclosed in commonly owned U.S. Pat. No. 9,392,941, which is incorporated herein by reference in its entirety.

By using an athletic activity monitoring system including one or more portable sensors, embodiments of the present invention described below may advantageously enable an individual (or a coach, a teammate, or a spectator) to obtain this or other information about the motion of an individual during the course of the athletic activity. Data obtained by sensors may be processed in a variety of ways to yield useful information about the activity of the individual.

FIG. 1A illustrates an exemplary monitoring system 100 that uses sensor devices $106_1$ and $106_2$ (collectively and generically referred to as sensor device(s) 106 herein) that have been embedded in articles of apparel. As shown in FIG. 1A, individual 102 is wearing items of apparel in which sensor devices $106_1$ and $106_2$ have been embedded. For instance, sensor device $106_1$ is embedded in a shoe worn by individual 102. Similarly, sensor device $106_2$ is embedded in a garment worn by individual 102. While not specifically shown here, sensor devices could also be embedded in other items of apparel (e.g., headbands, hats, wristbands, gloves, jackets, wetsuits, swimsuits, and vests, to name a few non-limiting examples). To obtain information about the actions of the individual 102 while wearing the apparel containing the sensor devices (e.g., devices $106_1$ and $106_2$), a wireless reader such as remote device 104 may be used to communicate with the sensor devices $106_1$ and $106_2$. In some embodiments, the mobile device 104 may communicate with sensor device $106_1$ and $106_2$ using near-field communication protocols.

While FIG. 1A depicts sensor device $106_1$ embedded in a shoe and sensor device $106_2$ embedded in a garment, there are a number of possible different applications and locations for which embedded sensor devices 106 may be appropriate. For instance, in some embodiments, sensor devices 106 may operate as textile integrated sweat and/or heat analyzers, washing temperature control tags, payment devices, access control devices, and/or for garment usage information collection. Additionally, sensor devices 106 may operate as a textile integrated step counter tag. In such applications, the sensor device 106 may be embedded in, for instance, the arm, chest, or neck areas of a garment such as a shirt. In such embodiments, the remote device 104 may operate to charge the embedded sensor device 106 before an activity or exercise and to read the sensor device 106 data after the exercise. According to various embodiments, a sensor device 106 may be embedded either removably or permanently in an article of apparel (e.g., clothing or shoes) or in an accessory or piece of athletic equipment (e.g., balls, bats, pads, racquets, clubs, bags, belts, headbands, and wristbands, to name a few non-limiting examples). For instance, in some embodiments sensor devices may be embedded or affixed to an item via, e.g., sewing, gluing, a pocket, integration during manufacturing, to name a few non-limiting examples.

In some embodiments, sensor devices 106 may function as textile integrated heart rate monitor tags. In such embodiments, one or more sensor devices 106 may be embedded in a garment that sits on the waist of individual 102 such as a belt or in a chest strap or bra, for example. Additionally, in these embodiments, the sensor devices 106 may be charged before an activity or exercise by the remote device 104 and the data generated by the sensor devices 106 may be read after the exercises. However, in some embodiments, it would also be possible to have sensor devices 106 regularly or continuously communicate sensor data to the remote device 104 in substantially real time using, e.g., NFC, Bluetooth, Bluetooth LE, WiFi, or any other suitable means of wireless communication. Additionally, in some embodiments, the sensor device 106 may include a flexible display integrated with a wrist or sleeve area of a garment of individual 102 with separate sensor devices 106 implementing ECG pads. The separate ECG pad sensor devices 106 may, in some embodiments, be integrated into a shirt or other garment worn at an appropriate location on an individual's 102 body.

Embodiments additionally include use of sensor devices 106 to monitor sleep. In such embodiments, the sensor devices 106 may be integrated with sleep garments such as pajamas or sleeping pants with the sensor devices located, for instance, in a waist area or chest area of the sleep garment. For sleep monitoring, sensor devices 106 could be configured to measure night movements, heart rate, and breathing and this data could be processed and used to generate a sleep quality indication.

According to various embodiments, the monitoring system 100 may be suitable for monitoring the activities of an individual 102 while performing a variety of different individual, team, or ordinary day-to-day activities. For example, monitoring system 100 according to embodiments of the present invention may be suitable for use by individuals 102 engaged in athletic activities such as baseball, basketball, bowling, boxing, cricket, cycling, football (i.e., American football), golf, hockey, lacrosse, rowing, rugby, running, skateboarding, skiing, soccer (i.e., football), surfing, swimming, table tennis, tennis, or volleyball, or during training sessions related thereto. In addition to its monitoring functions, system 100 may be useful for a number of other applications. These are described generally in FIG. 1B.

FIG. 1B is a block diagram depicting a system 110 that includes a sensor device 112 and one or more readers. In various embodiments, sensor device 112 may be similar to either of sensor devices 106 shown in FIG. 1A. And, like in FIG. 1A, FIG. 1B depicts the sensor device 112 communicating with a mobile device 118, which could be similar to the mobile device 104 depicted in FIG. 1A. However, the sensor device 112 of FIG. 1B is also configured to communicate with a payment reader 114, an access reader 116, and/or a wireless reader 120.

In various embodiments, the sensor device 112 may be associated with an account corresponding to a particular user (e.g., individual 102) and associated rights that correspond to that user. For instance, in some embodiments, when sensor device 112 may allow individual 102 to pay for purchases when it is used to communicate with payment reader 114 at, e.g., a point of sale. Additionally, in some embodiments, the sensor device 112 may provide access control functionality. For instance, when sensor device 112 communicates with an access reader 116, it may provide proper credentials to grant access to individual 102 to a controlled area or item. For example, the individual wearing a team uniform could be granted access to a locker room, practice facility, or playing field by virtue of being identified as an authorized team member. In some embodiments, the sensor device 112 may also provide identification functionality when used in conjunction with, e.g., wireless reader 120. This may have applicability in, for example, a marathon or other race where each runner is wearing an item of apparel that has a sensor device 112 embedded in it and can be identified using a wireless reader 120 that communicates with the sensor device 112.

In the system 110 depicted in FIG. 1B, each of the readers 114, 116, 118, and 120 may communicate with the sensor device 112 using near-field communication (NFC) protocols. In such embodiments, the readers 114, 116, 118, and 120 may power the sensor device 112 by wirelessly exciting an NFC circuit contained in the sensor device 112. Additionally, each of the readers 114, 116, 118, and 120 may be configured to engage in two-way communication with the sensor device. This kind of operation of the sensor device is described in greater detail with respect to FIG. 2

Figure 2:
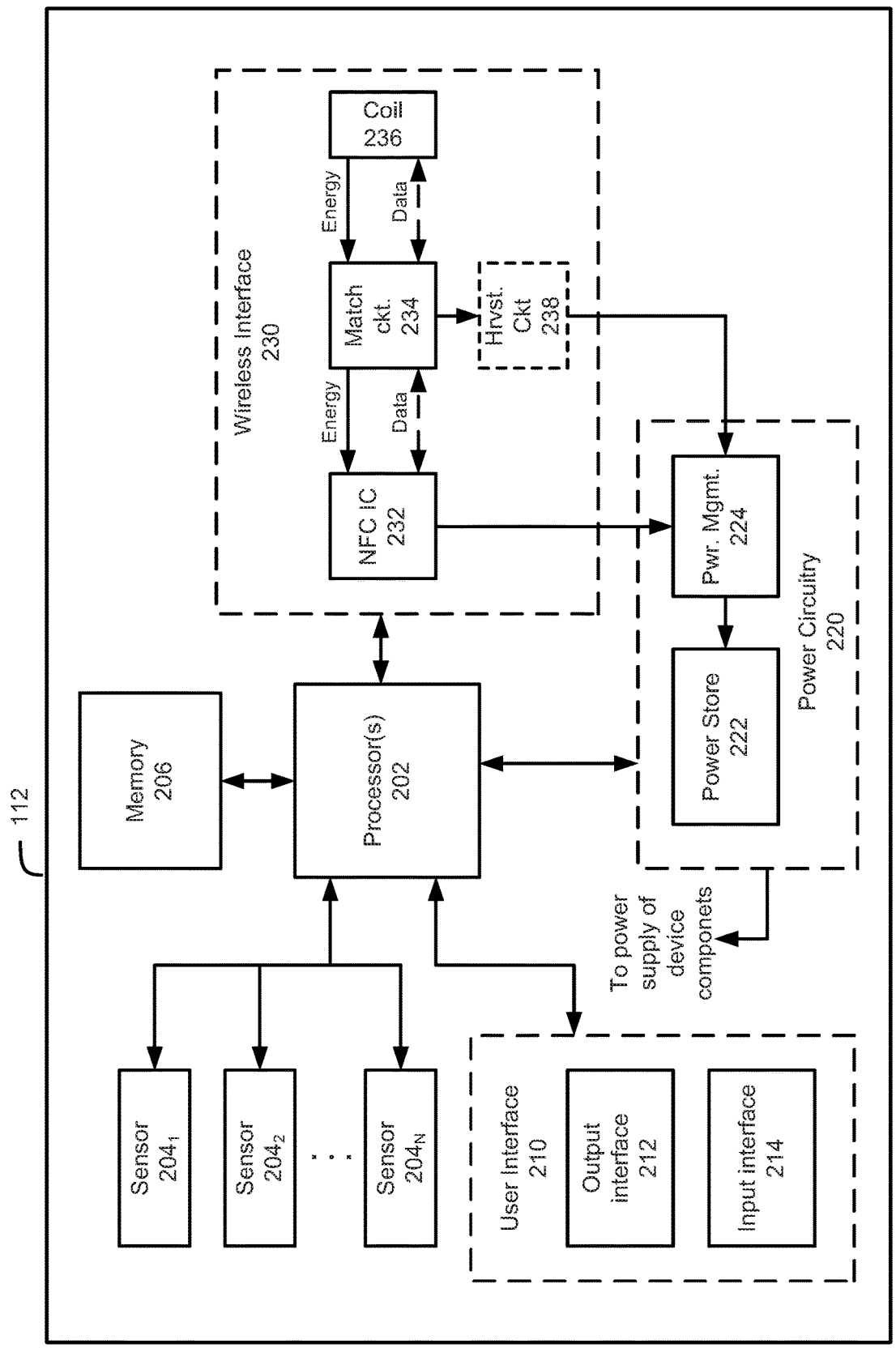
FIG. 2 is a block diagram depicting a sensor device according to an example embodiment.

FIG. 2 is a functional block diagram depicting an exemplary sensor device (e.g., sensor device 112) according to various embodiments. As can be seen, the sensor device 112 may comprise one or more processors 202, sensors 204, a memory 206, a user interface 210, power circuitry 220, and a wireless interface 230.

The one or more processors 202 may comprise, for instance, a microcontroller that is configured to process transmissions received from a remote device via the wireless interface 230, operate on the memory 206, and receive and process data from sensors 204. Additionally, the processors 202 may be powered by power circuitry 220. However, in some embodiments, processors 202 may have a separate dedicated power source.

Sensor device 112 also may include sensors $204_1$, $204_2$, ..., and $204_N$ (collectively referred to herein as "sensors 204"). While FIG. 2 depicts sensors 204 as being part of sensor device 112, in some embodiments sensors 204 may be external to sensor device 112. In some embodiments the sensors 204 may be part of the sensor device 112 when including of the sensors 204 at the sensor device 112 is practical or desirable because of size, weight, location, or durability characteristics. For example, including an accelerometer module near the chest position on a shirt may not impede the wearer and may generate acceptable data. In other embodiments, the sensors 204 may be external to sensor device 112 because of size, weight, location, or durability characteristics. For example, it may be desirable to have the sensor device 112 located on a wrist band or the wrist area of a shirt for ease of placing the a mobile device 118 in proximity to the sensor device 112, while at the same time it may be desirable to place heart rate sensors near the wearer's chest and accelerometers near the user's foot (e.g. in a shoe). Moreover, in some embodiments, sensors 204 may be changeable and/or replaceable depending on the particular application for which sensor device 112 will be used. Indeed, there are a number of different ways and/or positions may be employed in the various embodiments. In some embodiments, only one sensor may be employed, but in other embodiments, multiple sensors may be employed depending on the application. Additionally, as noted above, sensors may be placed in any relevant part of an item of apparel, equipment, clothing, shoes, etc.

Sensors 204 may be configured to communicate with processor 202 via a communication channel either in serial or in parallel using any appropriate communication method such as Inter-Integrated Circuit (I²C) bus, a SCSI Parallel Interface (SPI), and/or a universal asynchronous receiver/transmitter (UART), to name a few non-limiting examples.

In various embodiments, sensors may include sensors for measuring: heart rate (ECG and/or PBG based); a maximum volume of oxygen used; steps, speed, pace, distance, acceleration, temperature, moisture, conductivity, ambient light, ultra violet light, sound, breathing rate, muscle contraction, breathing pattern, altitude, pressure, sweat, or any other measureable parameters, to name a few examples.

Memory 206 may be non-volatile memory that is capable of storing raw data from sensors 204 and/or the results of calculations performed by processors 202. Additionally, the memory may store any of a number of parameters (e.g., user personalization parameters such as account identification, access rights, height, weight, gender, etc.) for use by the processors 202. According to various embodiments, memory 206 may be constructed from any suitable type of memory or combination of types of memory such as random access memory (RAM), read only memory (ROM), erasable programmable read-only memory (EPROM), electrically erasable programmable read-only memory (EEPROM), Flash memory, magnetic memory, optical memory, or the like, to name some non-limiting examples. Additionally, the memory 206 may communicate with the microcontroller via I²C, SPI, UART, or any other suitable serial or parallel communication method.

According to some embodiments, the sensor device 112 may also be equipped with "hidden" features that cannot be accessed unless unlocked. In some embodiments, the status (i.e., whether they are locked or unlocked) of the "hidden" features may be stored in the memory. For instance, in some embodiments, the "hidden" features by be activated by a communication from one or more remote device (e.g., one of readers 114, 116, 118, or 120). By way of example, consider a case where sensor device 112 is embedded in a pair of shoes, as is shown in FIG. 1A with respect to sensor device 106. It may be possible to have hidden features (e.g., the calculation of metrics that are relevant to runners) remain locked until they are specifically unlocked by communication with a reader (114, 116, 118, or 120). Once unlocked, the sensor device 112 and/or 106 may be enabled to perform the specialized calculations and subsequently make them available to the individual 102 via mobile device 118.

The sensor device 112 may also include a user interface 210. The user interface may include either or both of an output interface 212 and an input interface 214. The output interface 212 may be configured to communicate information to individual 102. For instance, in some embodiments, the output interface 212 may be a display or indicator. In such embodiments, the display may comprise one or more display devices (e.g., LEDs, OLEDs, LCDs, etc.) and can be used to indicate, for instance, a charging level, a step count, a heart rate, or any of a number of other possible items. In some instances, the display may output calculated values based on sensor data from sensors 204 that has been calculated by processors 202.

The user interface 210 may also include an input interface 214. The input interface may comprise one or more buttons, switches, capacitive touch devices, or any suitable means for allowing a user such as individual 102 to interact with sensor device 112. In some embodiments, a user may toggle between different display options using the input interface 214. Additionally, user approval of an action taken by sensor device (e.g., transmitting stored data to a remote device) may be received via input interface 214 prior to the action being taken.

The power circuitry 220 may provide power to the various components of sensor device 112. As shown in FIG. 2, power circuitry 220 includes a power store 222 and management circuitry 224. The power store 222 may include one or more of a battery, capacitor, super capacitor, or hybrid capacitor and can be used as the main power supply for the system. Additionally, the power store 222 can be charged via the power management circuitry 224.

According to various embodiments, the power management circuitry 224 may be used to charge the power store 222 and to manage power flow during charging and usage. During a charging cycle, the power management circuitry may be configured to monitor the charge stored on the power store 222 and to cut charging when the charge on the power store 222 has exceeded a predetermined safety threshold for the power store 222. During normal usage (i.e., non-charging), the power management circuitry 224 may also monitor the voltage of the power store 222 and cut the power when the voltage on the power store 222 falls below a predetermined level. In some embodiments, the power management circuitry 224 may be responsible for providing power to each of the various components of sensor device 112.

Wireless interface 230 is responsible for receiving power from and transmitting data to/from a remote device (e.g., one or more of readers 114, 116, 118, and 120). As shown in FIG. 2, the wireless interface 230 may comprise an NFC circuit 232, a matching circuit 234, and a coil 236. Additionally, in some embodiments, the wireless interface 230 may include optional harvesting circuitry 238.

The NFC circuit 232 may comprise one or more integrated circuits that manage NFC data transmission between sensor device 112 and a remote device (e.g., readers 114, 116, 118, and 120) through means of inductive interaction. In some embodiments, the NFC circuit 232 may also be configured to harvest energy from an NFC signal transmitted by a remote device. However, in some embodiments, the harvesting of energy may also or instead be performed by separate harvesting circuitry 238. The harvesting circuitry may include appropriate harvesting circuit components such as a rectifier, capacitor, and a voltage detector.

Matching components 234 may be used to adjust the frequency band of signals to resonance with the frequency used by the transmitter of a remote device. For instance, when NFC is being used, the matching components could be adjusted to the NFC frequency of 13.54 MHz. According to some embodiments, the matching circuitry may be dynamic and able to match to multiple frequencies.

Coil 236 may comprise one or more coils for use in data transmission and wireless power transfer from a remote device (e.g., readers 114, 116, 118, and 120). In some embodiments, the coil 236 may be integrated into a printed circuit board of the sensor device 112. However coil 236 may also be implemented as one or more separate coils in some embodiments. In some embodiments, the coil 236 may have an inductance between 0.5 µF and 2.5 µF.

Figure 3:
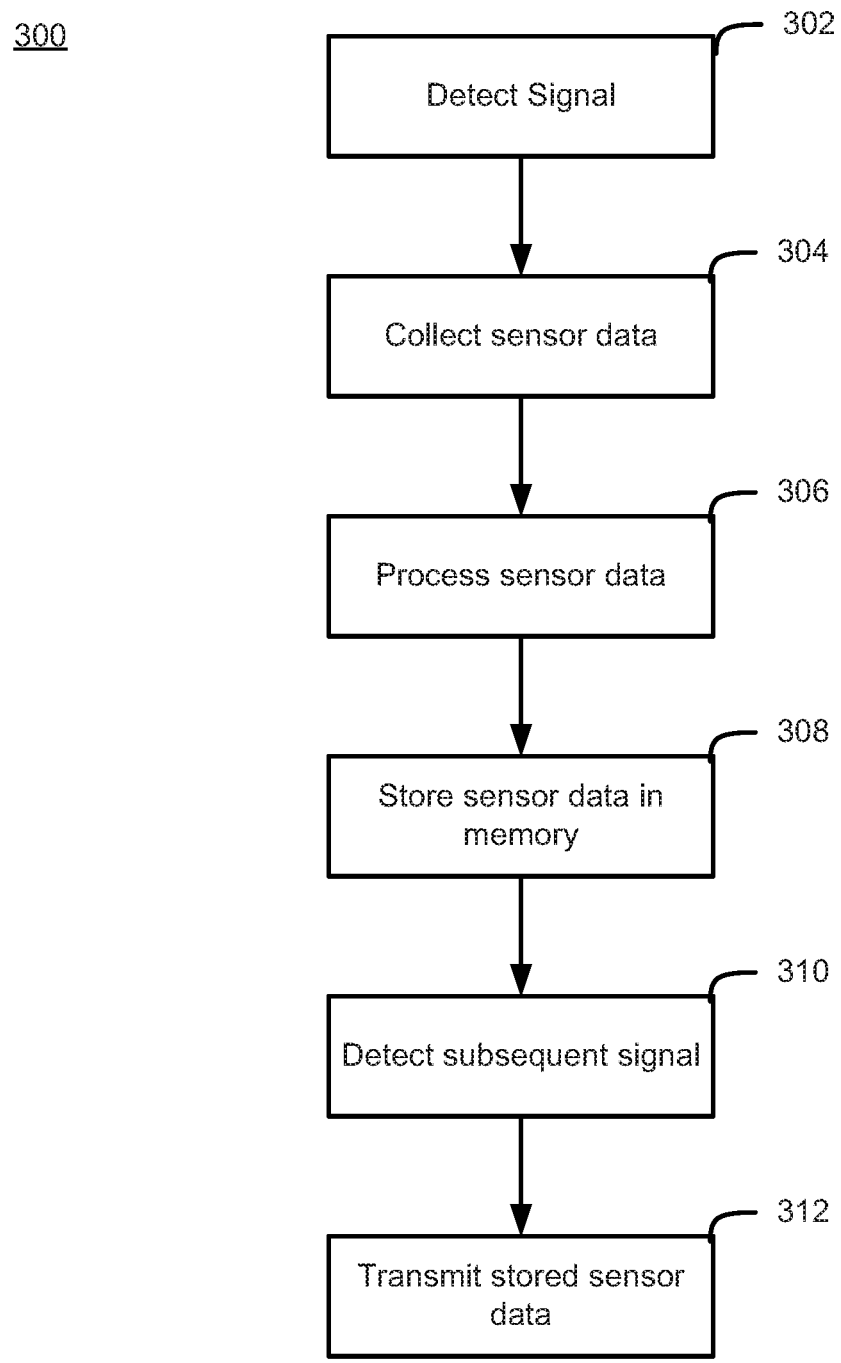
FIG. 3 is a flowchart illustrating a method of collecting sensor data from a sensor device according to various embodiments.

FIG. 3 is a flowchart depicting a method 300 of collecting sensor data according to various embodiments. For ease of explanation, FIG. 3 will be described with respect to FIGS. 1A, 1B, and 2. However, it should be understood that this is just for convenience and that the method depicted in FIG. 3 should not be construed as being limited to those specific embodiments.

As shown in FIG. 3, method 300 begins at 302 when a signal from a reader (e.g., device 104) is detected by the sensor device 112. According to various embodiments, this first signal detected by the sensor device 112 may contain data as well as power, which can be harvested from the signal via inductive coupling by the wireless interface 230. The harvested power can then be used by power circuitry 220 to charge the power store 222.

At 304, after detecting the signal, the sensor device 112 may be configured to begin collecting raw sensor data from sensors 204. For instance, the one or more sensors may collect a variety of different data elements (e.g., heart rate (ECG and/or PBG based); a maximum volume of oxygen used; steps, speed, pace, distance, acceleration, temperature, moisture, conductivity, ambient light, ultra violet light, sound, breathing rate, muscle contraction, breathing pattern, altitude, pressure, sweat, etc.). The raw data elements from sensors 204 may then be conveyed to the processors 202 for processing at 306. At 308, the processors 202 may store either or both of the raw data elements from the sensors or processed values based on the raw values in memory 206.

Upon detecting a subsequent signal from a remote device (e.g., mobile device 104), at 310, the sensor device 112 may be configured to transmit some or all of the data stored in memory (e.g., either or both of the raw data elements from the sensors or processed values based on the raw values in memory 206) to the remote device at 312. According to some embodiments, one or more of the signals received from remote device 104 by the sensor device 112 may also be used to provide power and/or charge the power store 222 of the sensor device. 112. Additionally, in some embodiments, whenever a remote device comes in to close proximity with the sensor device 112 (i.e., it is "tapped"), then the remote device may transmit energy to the sensor device allowing sensor device 112 to power its processor(s) 202 such that they can perform calculations on raw data collected from sensors 204. This can enable the sensor device 112 to transmit finished data to the remote device instead of raw data without using energy stored in the sensor device 112. In some embodiments, the sensor device 112 may also and/or instead transmit the raw data. A method of operating such embodiments is described with respect to FIG. 4, below.

Figure 4:
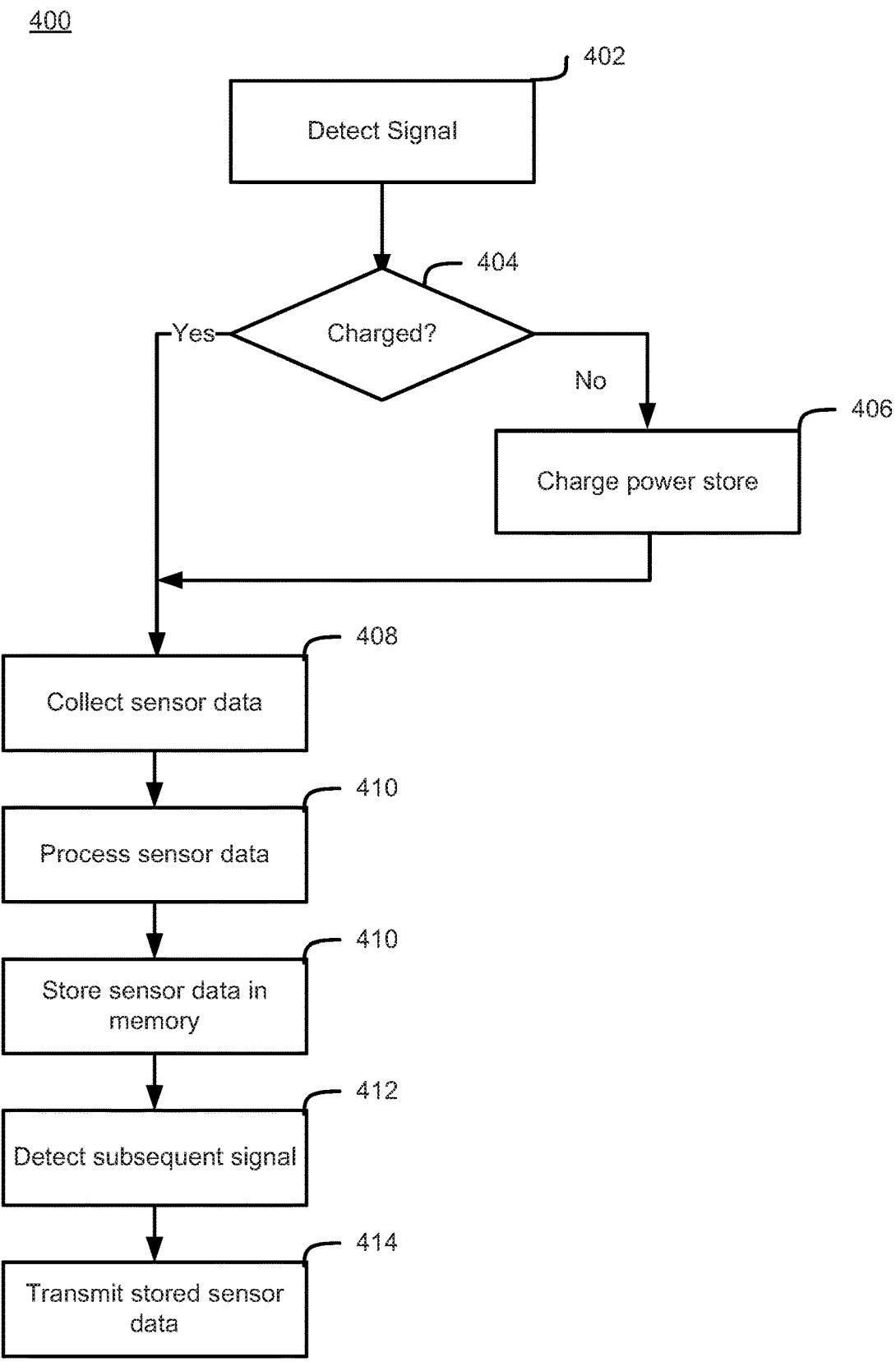
FIG. 4 is a flowchart illustrating a method of collecting sensor data from a sensor device according to various embodiments.

FIG. 4 is a flowchart depicting a method 400 of collecting sensor data and charging a sensor device 112 according to various embodiments. As was the case for FIG. 3, FIG. 4 will be described with respect to FIGS. 1A, 1B, and 2. However, it should be understood that this is just for convenience and that the method depicted in FIG. 4 should not be construed as being limited to those specific embodiments.

As shown in FIG. 3, method 400 begins at 402 when a signal from a remote device (e.g., device 104) is detected by the sensor device 112. According to various embodiments, this first signal detected by the sensor device 112 may contain data as well as power, which can be harvested from the signal via inductive coupling by the wireless interface 230. The harvested power can then be used by power circuitry 220 to charge the power store 222.

At 404, the sensor device 112 determines whether it has sufficient stored power it its power store. If not, then at 406, the sensor device may inductively charge its power store 222 using power circuitry and either the NFC circuit 232 or the separate harvesting circuit 238 to obtain power from the signal transmitted by the remote device 104. After charging the power store, the method 400 proceeds to 408. In some embodiments, charging may occur every single time the sensor device 112 is in close proximity with the remote device 104 (i.e., "tapped") and/or can end when the power store 222 is full. Additionally, data transmission to/from remote device 104 may occur simultaneously with power transmission from the remote device 104, though in some embodiments data transmission and power transmission may occur independently.

At 308, after detecting the signal and/or charging the power store, the sensor device 112 may be configured to begin collecting raw sensor data from sensors 204. For instance, the one or more sensors may collect a variety of different data elements (e.g., heart rate (ECG and/or PBG based); a maximum volume of oxygen used; steps, speed, distance, acceleration, temperature, moisture, conductivity, ambient light, ultra violet light, sound, breathing rate, muscle contraction, breathing pattern, altitude, pressure, sweat, etc.). The raw data elements from sensors 204 may then be conveyed to the processors 202 for processing at 410. At 412, the processors 202 may store either or both of the raw data elements from the sensors or processed values based on the raw values in memory 206.

Upon detecting a subsequent signal from a remote device (e.g., mobile device 104), at 412, the sensor device 112 may be configured to transmit some or all of the data stored in memory (e.g., either or both of the raw data elements from the sensors or processed values based on the raw values in memory 206) to the remote device at 414.

In some embodiments, the remote device (e.g., device 104) can be configured to wirelessly transmit an appropriate amount of power to the sensor device 112 depending on the kind of activity that is to be monitored by the sensor device 112. Since the amount of power transmitted to the sensor device is a function of the duration of the transmission, once it has determined the power required by the sensor device 112, the remote device 104 can transmit for the appropriate amount of time in order to transfer enough power to the sensor device 112. For instance, in one test example it was found that a remote device 104 needed to charge for the following durations in order to provide sufficient power to the sensor device 112 for the following activities:

| Usage Scenario | Maximum Charging time per hour of activity |
| --- | --- |
| All day activity tracking and movement detection (no heart rate) + temperature logging | 2 seconds |

-continued

| Usage Scenario | Maximum Charging time per hour of activity |
|---|---|
| All day activity tracking and movement detection (with heart rate) | 20 seconds |
| Speed and distance measurement with accelerometer (no heart rate) | 40 seconds |
| Speed and distance measurement with accelerometer (with heart rate) | 60 seconds |

In some embodiments, the sensor device 112 is configured such that a sufficient charge to power the device for necessary monitoring can be achieved in sixty seconds or less. In other embodiments, the sensor device 112 is configured such that a sufficient charge to power the device for necessary monitoring can be achieved in forty seconds or less, thirty seconds or less, twenty seconds or less, ten seconds or less, five seconds or less, two seconds or less, or one second or less. In some embodiments, data transmission by the sensor device 112 is suspended while the sensor device is being charged in order to reduce the amount of time it takes to charge the sensor device 112.

Figure 5:
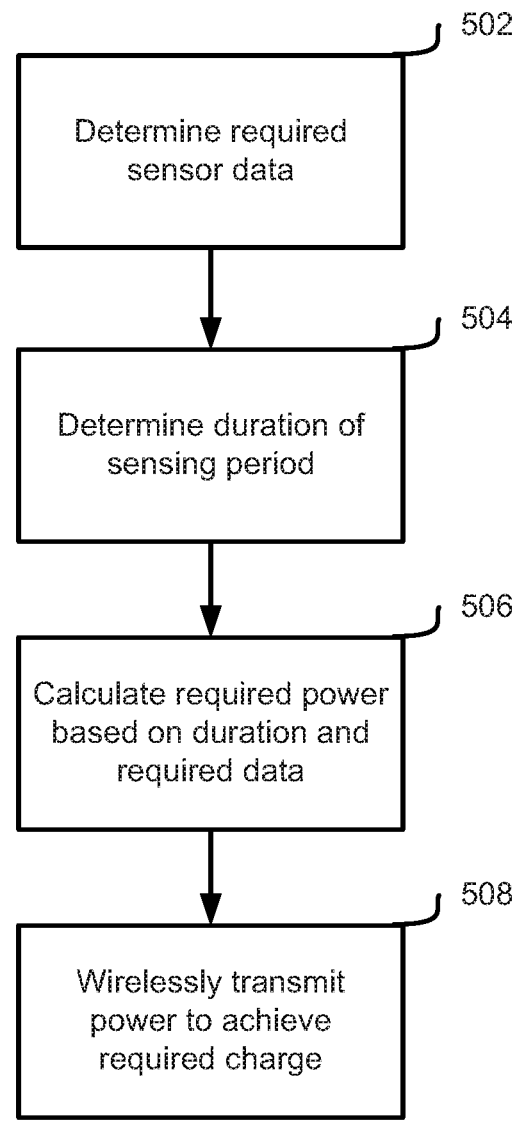
FIG. 5 is a flowchart illustrating a method of collecting sensor data from a sensor device according to various embodiments.

FIG. 5 is a flowchart depicting a method 500 that a remote device (e.g., device 104) can use to transmit the appropriate amount of power to a sensor device (e.g., sensor device 112) according to various embodiments. FIG. 5 will be described with respect to FIGS. 1A, 1B, and 2. However, it should be understood that this is just for convenience and that the method depicted in FIG. 5 should not be construed as being limited to those specific embodiments.

As shown in FIG. 5, method 500 begins at 502 where the remote device 104 determines which sensor data the sensor device 112 will be required to collect. This could be based on a number of factors. For instance, in one embodiment, each sensor device may be pre-configured to always collect the same sensor data. In other embodiments, a user may enter desired sensor data to be collected into the remote device 104. In another embodiment, a user of an activity monitoring app running on the remote device 104 (e.g. a mobile phone) may be executing a particular training plan or workout routine on the activity monitoring app that may dictate the type of sensor data to be obtained. Suitable software apps may include, for example, those disclosed in commonly owned U.S. Pat. No. 9,392,941, which is incorporated herein by reference in its entirety.

By way of example, consider an embodiment where the sensor device is capable of collecting speed, distance, and heart rate data. In such an example, a user (or their app) might request that the speed and distance be collected, but not heart rate data. The remote device 104 might, therefore, be configured to use this input to determine that only speed and distance data need to be collected by the sensor device at 502. Additionally, in some embodiments, a user may select from a menu of pre-determined sensor configurations suited for a particular activity. In this example, the user might select from categories such as: running, hiking, bicycling, sleeping, etc. Based on the selected category, the remote device 104 may be configured to determine the required sensors and sensor data for the sensor device 112.

At 504, the remote device 104 may determine a duration of the sensing period. According to some embodiments, the determination may be based on a user input to the remote device 104 indicating the duration of the activity or exercise in which the user (e.g., individual 102) will engage. Additionally, it may be possible for the remote device to determine the duration based on pre-set values for particular categories of activities selected by the user. For instance, if sleep monitoring is the activity indicated by the user, then remote device may default to a duration of 8 hours. In another example, the remote device may default or may be programmed to a duration equal to an amount of time sufficient to capture data from a predetermined activity such as a run, a slow walk or bike ride (e.g. a walk or bike ride commute to work), an individual athletic event such as a race, or a team athletic event such as a basketball or soccer game. Additionally, in some embodiments, the user may not be required to enter a duration at all and the remote device 104 may default to a pre-determined maximum duration.

At 506, the remote device 104 may calculate the required power needed by the sensor device 112 based on the kind of sensor data determined at step 502 and the duration of the sensing period determined at step 504. In some embodiments, the values of the required charge may be stored in memory elements of the remote device 104 and may, for instance, be organized in the form of a look-up-table or the like. Some embodiments may also or instead calculate the number based on known power usage figures for the various sensors that will be used by the sensor device 112 for the task at hand. For instance, the remote device may know the average power usage rate per unit time for a particular sensor element. By multiplying that number by the duration of the sensing period, the remote device may calculate the total amount of power that will be required for the task at hand. In other embodiments, the calculation may involve factoring in the average power usage rate per unit time averaged among a plurality of modes that the sensor element is likely to, or has historically operated according to, embodiments where the sensor element has different operation modes. Operation modes may be, for example, different sensing modes or power consumption modes.

At 508, the remote device may be configured to wirelessly transmit the power to sensor device 112, which can harvest it using inductive elements contained in the wireless interface 230 of the sensor device 112. According to embodiments, the amount of power transmitted is a function of the length of the transmission time. Accordingly, the remote device 104 may be configured to transmit its signal to the sensor device 112 for an appropriate amount of time to transfer the required power calculated at 506.

Figure 6A:
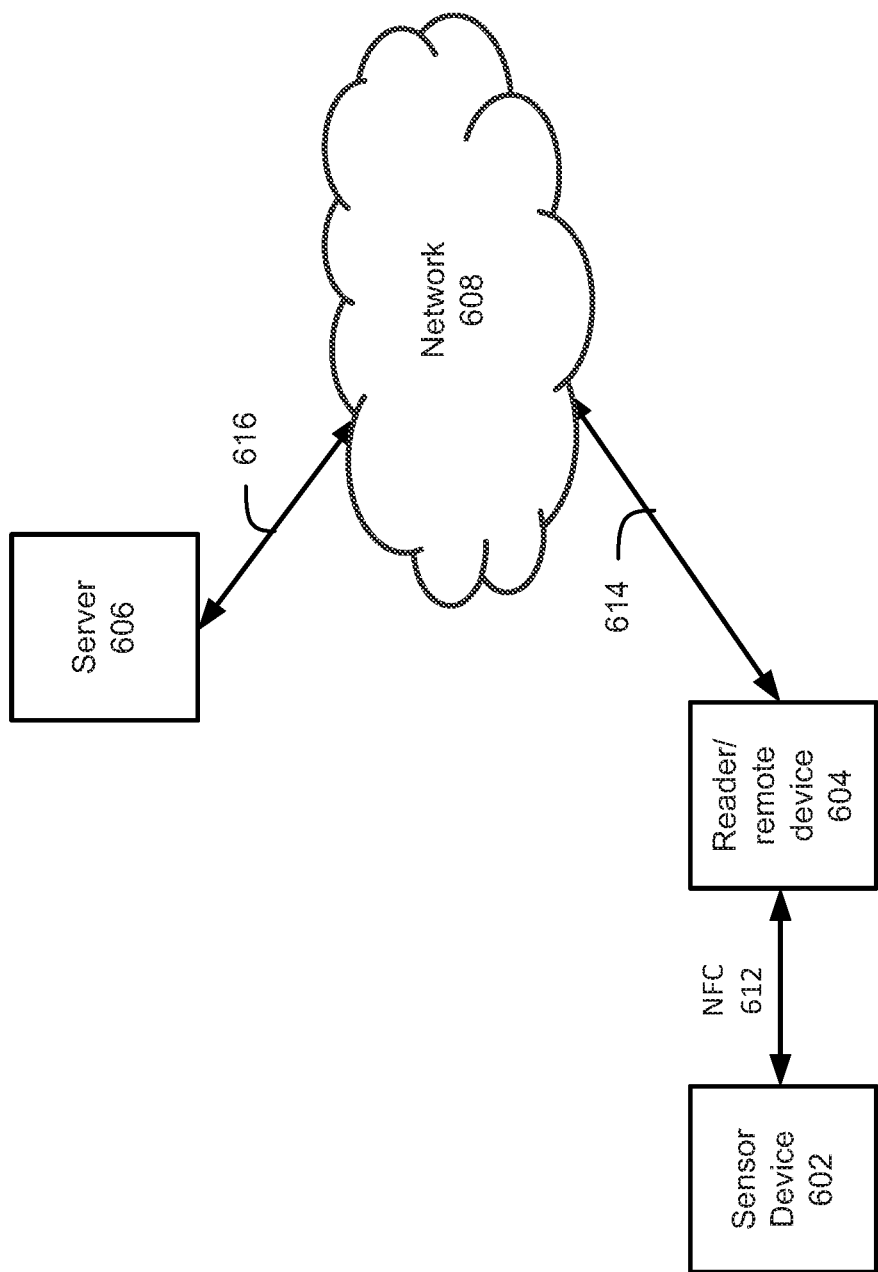
FIG. 6A is a block diagram depicting a network system that includes a sensor device according to various embodiments.
Figure 6B:
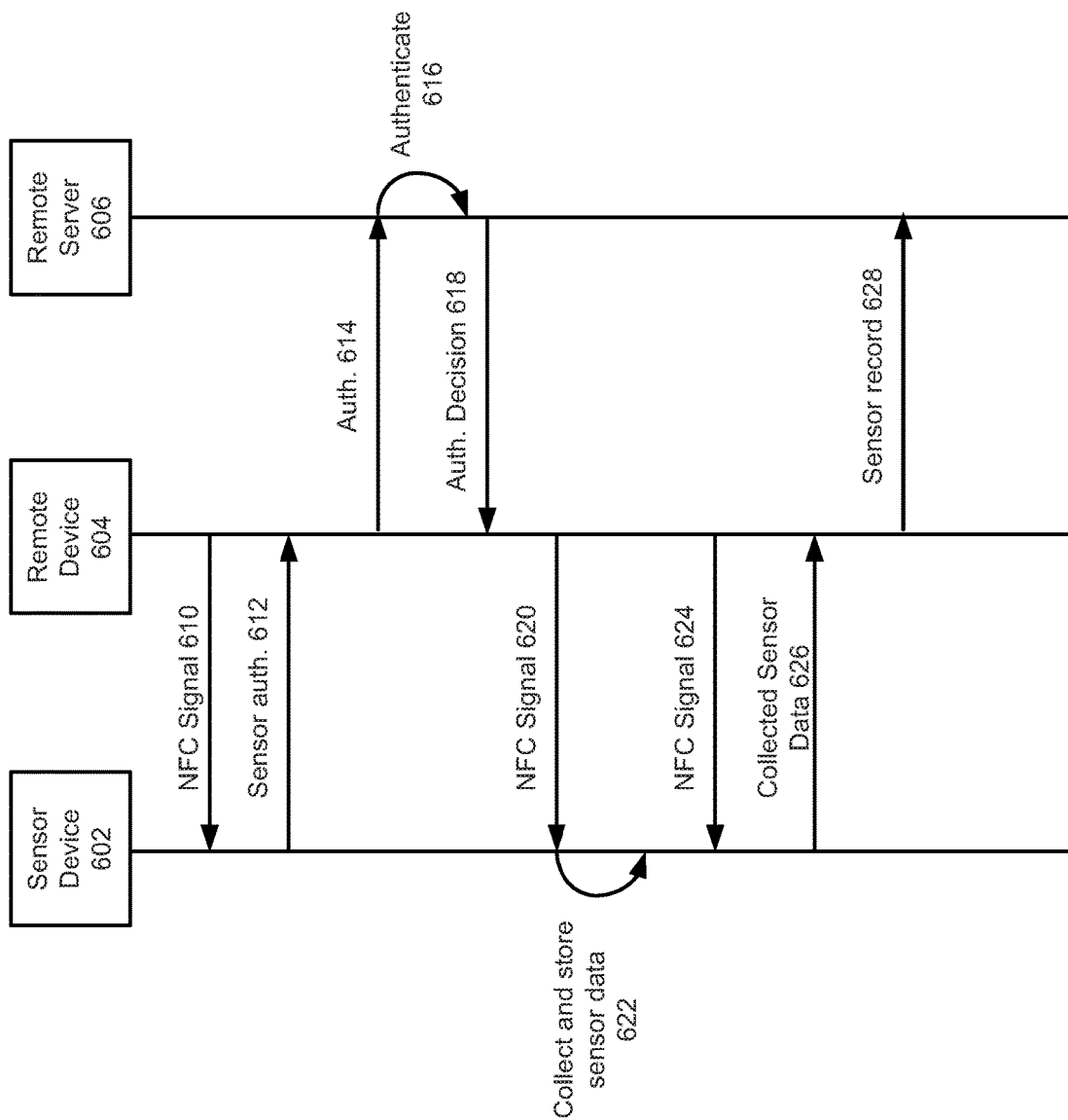
FIG. 6B is a sequence chart illustrating communication between components of a network system that includes a sensor device according to various embodiments.

In some embodiments, it may be possible to transmit sensor data from a sensor device to a remote server for storage and analysis. Such a system is shown in FIGS. 6A and B. FIG. 6A is a block diagram depicting a system 600 capable of storing sensor data remotely from a sensor device according to various embodiments. FIG. 6 will be described with respect to FIGS. 1A, 1B, and 2. However, it should be understood that this is just for convenience and that the method depicted in FIGS. 6A and 6B should not be construed as being limited to those specific embodiments.

As shown in FIG. 6A, the system 600 may include a sensor device 602, a reader/remote device 604, and a remote server 606 that is communicatively coupled to the remote device 604 via a network 608 such as the internet. Sensor device 602 may be any suitable sensor device for embedding in a garment, such as sensor devices 106 or 112. Reader/remote device 604 may be any suitable reader (e.g., any of readers 114, 116, 118, and 118) capable of transmitting and receiving data to and from the sensor device 602. In some embodiments, the reader/remote device 604 may comprise a device with NFC capabilities, such as a smartphone, such that an NFC channel 612 can be established between the reader/remote device 604 and the sensor device 602. The reader/remote device 604 may communicate with server 606 via a network 608 such as the internet using communications channels 614 and 616. Communications channels 614 and 616 may comprise any suitable communication channels such as wired Ethernet, cellular, IEEE 802.11, Bluetooth, and Bluetooth LE, to name a few non-limiting examples.

FIG. 6B is a sequence diagram illustrating how the sensor device 602, reader/remote device 604, and the remote server 606 of system 600 may communicate with each other according to various embodiments. As shown in FIG. 6B, the remote device 604 may transmit a signal (e.g., an NFC signal) 610 to sensor device 602. Upon receiving signal 610 from the remote device 604, in some embodiments, the sensor device may transmit sensor authentication information 612 to the remote device 604.

The remote device 604 may then transmit an authentication request 614 to the remote server 606. The authentication message 614 may simply be the sensor authentication information 612 unaltered, in some embodiments. However, in other embodiments, the authentication message may include both the sensor authentication information 612 as well as additional authentication information (e.g., user account information, device identification information, payment information, or other relevant information, to name a few non-limiting examples). Upon receipt of the authentication request 614, the remote server may perform authentication 616 of either or both of the sensor device 602 and the remote device 604. After performing authentication 616, the remote server 606 may transmit an authentication decision 618 to the remote device 604.

In some embodiments, the device authentication request 614 and device authentication 616 can be used as theft prevention. For instance, if an article of apparel with an embedded sensor device 112 is stolen, the owner of the apparel could report the theft to a service provider (e.g., remote server 606), which could flag the associated article of apparel and/or the sensor device 112 as stolen and remove all authentication for use of the stolen article of apparel—effectively rendering the sensor device 112 associated with the stolen article useless.

In some embodiments, this process can be reversed if a lost or stolen article of apparel is subsequently recovered. When an article is recovered, the owner can report the recovery to the service provider (e.g., remote server 606) and the service provider can then remove the lost or stolen flag from the item. In this scenario, the next time an attempt to authenticate the article of apparel is made, it should be successful.

If one or both of the sensor device 602 and the remote device 604 could not be authenticated, then the remote device 604 may be prevented from using some or all of the functionality of the sensor device 602. For instance, consider an example where one or more of the sensors 204 of sensor device are "premium" add-on sensors that are available only with authentication. In such a situation, the sensor device 602 may require a unique code or ID from the remote server 606 in order to activate the "premium" sensors. Without the unique code or ID from the remote server 606, the "premium" sensors will not function. In this way, the remote server 606 may keep un-authenticated remote devices 604 and sensor device 602 from accessing the "premium" sensors by withholding the unique code or ID. This restricted access to the "premium" sensors can, for instance, be used by service providers as an incentive to users to register a sensor device 112 or subscribe to additional services offered by a service provider.

Upon receipt of the authentication decision 618, the remote device may transmit another signal 620 (e.g., an NFC signal) to the sensor device 602. Signal 620 may include information indicating which sensors should collect data and for how long. Additionally, signal 620 may also include any unique codes or IDs necessary to activate one or more sensors 204 of the sensor device 602. The sensor device 602 may then proceed to collect and store sensor data 622 (as, for instance, discussed with respect to FIGS. 3 and 4).

The remote device 604 may then transmit a signal 624 (e.g., an NFC signal) to sensor device 602. Upon receipt of the signal 624, the sensor device 602 may transmit collected sensor data 626 to the remote device 604. In some embodiments, signal 624 may define a subset of sensor data to be sent to remote device 604 as part of the collected sensor data 624. However, it is also possible for the sensor device 602 to transmit all saved sensor data as the collected sensor data 626. Upon receipt of the collected sensor data 626, the remote device 604 may transmit a sensor record 628 to the remote server 606 via, e.g., network 608. In some embodiments, the sensor record 628 may simply comprise the collected sensor data 626. However, it is also possible that the remote device may perform further processing on the collected sensor data 626 and that the sensor record 628 may be the result of the further processing. Additionally, the sensor record may also consist of multiple iterations of collected sensor data 626 taken, for instance, over multiple instances of an activity (e.g., an entire week's worth of sleep monitoring data, or an entire week's worth or workout records, possibly in accordance with a predetermined workout plan). When it receives the sensor record 628, the remote server 606 may perform further analysis and/or calculations on the sensor data and may also store the data for use at a later date by, for example, the user.

In some embodiments the sensor device 112 may be prompted to send the sensor record 628 to the remote device 604 under several different scenarios. For instance, the sensor device may be configured to begin recording after a first "tap" from the remote device 604 and then configured to send the sensor record 628 upon the second "tap." In some embodiments, as noted above, sensor may be configured to automatically transmit record data 628 at pre-determined (e.g., by user input) time intervals or at certain metric milestones (e.g., X number of steps, or Y distance, etc.) Additionally, the sensor device 112 in some embodiments may be configured to transmit sensor record 628 based on a recognized pattern of movement (e.g. a jump movement), and/or speed that corresponds to known start and ending patterns of movement, and/or speed. The sensor device 112 may also be configured to automatically start and end its recording based on similar parameters so that only "real" work out data is collected and/or calculated.

Figure 7:
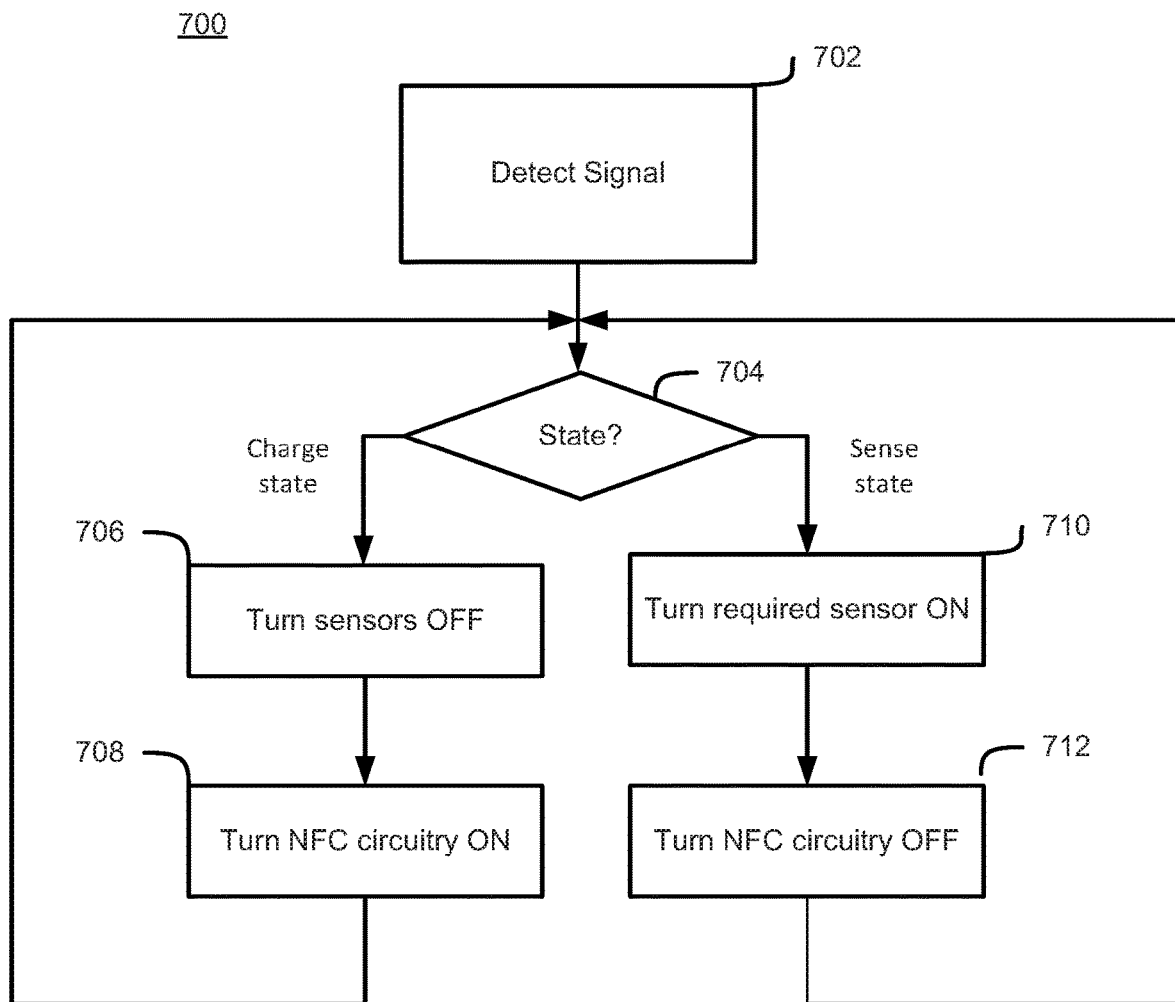
FIG. 7 is a flowchart illustrating a method of operating a sensor device according to various embodiments.

Because power may be at a premium for the sensor devices 112, methods of minimizing power usage can be important. As such, the sensor devices 112 may be configured to set various states. FIG. 7 displays a method 700 for reducing power usage in sensor devices 106 according to various embodiments. FIG. 7 will be described with respect to FIGS. 1A, 1B, and 2. However, it should be understood that this is just for convenience and that the method depicted in FIG. 7 should not be construed as being limited to those specific embodiments.

As shown in FIG. 7, the method 700 may begin at 702 where a sensor device 112 detects a signal (e.g., an NFC signal) from a remote device 104. In some embodiments, the detected signal may contain information that causes the sensor device 112 to set a state. For instance, when the signal indicates that it will charge the device, the state of the sensor device 112 could be set to a charging state. Conversely, when the signal detected at 702 indicates that the sensing device 112 will not be charging and will, instead, be collecting sensor data, the sensing device 112 may set a sensing state. Setting the state may comprise setting a flag or a value in a register of processors 202 and/or storing a value in memory 206. After receiving the signal, the sensor device 112 may determine what state it is in at 704. In some embodiments, determining the state may comprise reading the value of a state flag from the register of processors 202 or memory 206, for instance.

If at 704, the method determines that the sensor device 112 is in a sense state, then sensor device 112 may be configured to turn one or more sensors ON at 710. In some embodiments, turning the sensors ON may comprise providing power to the sensors from the power circuitry 220. It is also possible, however, that turning the one or more sensors ON may comprise sending one or more signals to the sensors 204 from, for instance, the processors 202. Additionally, when the sensor device 112 determines that it is in a sense state at 704, the sensing device 112 may also turn NFC circuitry OFF. In some embodiments, turning the NFC circuitry OFF may comprise cutting off power to the components of the wireless interface 230 from the power circuitry 220. However, turning NFC circuitry OFF may also comprise sending a signal from processors 202 to wireless interface 230 instructing one or more of the components of the wireless interface 230 to power down. While FIG. 7 shows 710 and 712 in a particular order, they need not be performed in the order depicted—indeed, they could be performed in the reverse order or in parallel in various embodiments. After 712, the method 700 may loop back to 704.

If, at 704, the sensor device 112 determines that it is in a charge state, then the sensor device may proceed to 706, where one or more sensors are turned OFF. In some embodiments, this may comprise turning all of the sensors OFF, but that need not be the case in every embodiment. Turning one or more sensors OFF may comprise removing power from the sensors 204 by the power circuitry 220. It is also possible, however, that turning the one or more sensors OFF may comprise sending one or more signals to the sensors 204 from, for instance, the processors 202. At 708, when the sensor device 112 detects that it is in a charge state, the sensor device 112 may turn NFC circuitry ON. In some embodiments, turning the NFC circuitry ON may comprise providing power to the components of wireless interface 230 from the power circuitry 220. It is also possible, however, that turning the NFC circuitry ON may comprise sending one or more signals to the wireless interface 230 from, for instance, the processors 202. While FIG. 7 shows 706 and 708 in a particular order, they need not be performed in the order depicted—indeed, they could be performed in the reverse order or in parallel in various embodiments. After 708, the method 700 may loop back to 704.

Figure 8:
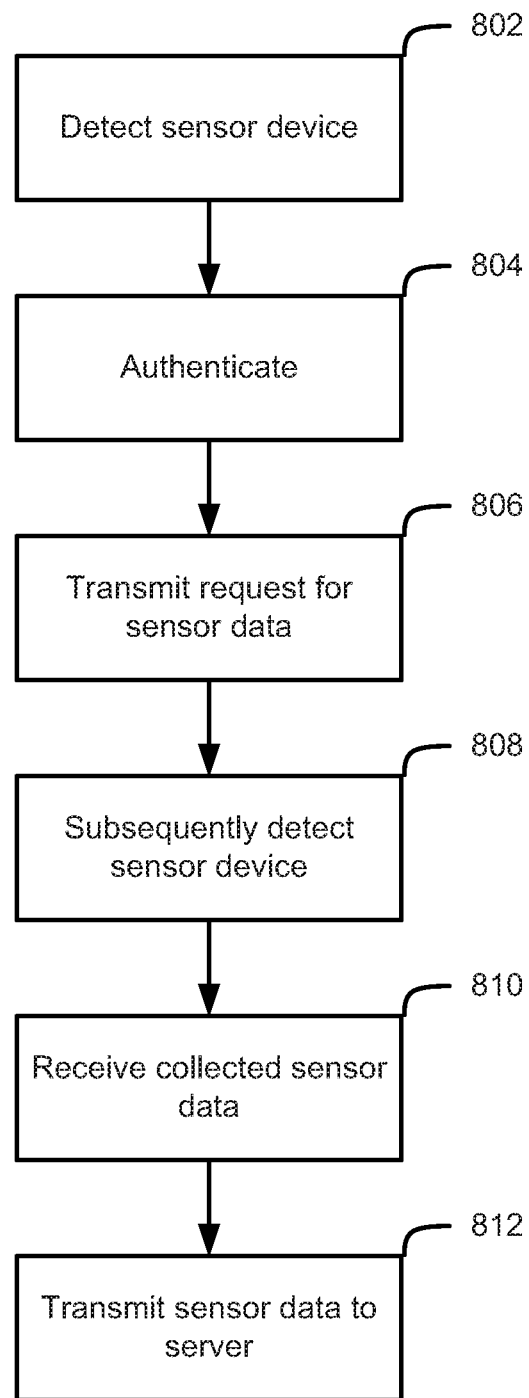
FIG. 8 is a flowchart illustrating a method of authenticating and collecting sensor data from a sensor device according to various embodiments.

FIG. 8 is a flowchart illustrating a method 800 of interacting with a sensor device (e.g., sensor device 112) using a remote device (e.g., remote device 104, such as a smart phone). FIG. 8 will be described with respect to FIGS. 1A, 1B, 2, and FIGS. 6A and 6B. However, it should be understood that this is just for convenience and that the method depicted in FIG. 8 should not be construed as being limited to those specific embodiments.

As shown in FIG. 8, the method 800 may begin when a remote device 104 detects a sensor device 112 at 802. In some embodiments, the remote device 104 may passively detect the sensor device 112 by transmissions emanating from the sensor device 112. However, the remote device 104 may also actively search for sensor device 112 by transmitting a signal (e.g., an NFC signal) that will activate sensor device 112. Additionally, in some embodiments, detection of the sensor device 112 may be triggered by placing the remote device 104 in proximity to the sensor device 112. A user may choose to place the remote device 104, such as a smart phone, in proximity to the sensor device 112 just prior to engaging in an athletic activity, such as going for a run.

In response to detecting the sensor device at 802, the remote device 104 may perform authentication at 804. In some embodiments, the authentication may comprise the authentication steps discussed with respect to FIG. 6B. After authenticating the sensor device 112, the remote device 104 may transmit a request for sensor data to the sensor device at 806. In some embodiments, the request for sensor data may comprise information identifying specific sensors from which data will be requested and/or a duration of sensing activity.

At 808, the remote device 104 may subsequently detect the sensor device 112 again. This may occur, for example, when a user places the remote device 104, such as a smart phone, in proximity to the sensor device 112 just after completing an athletic activity, such as going for a run. Again, the remote device 104 may either passively or actively detect the sensor device 112, as discussed above. Upon detection, the remote device 104 may trigger the sensor device to transmit sensor data to the remote device 104 and the remote device 104 may receive the collected sensor data at 810. In some embodiments, the remote device may subsequently transmit sensor data to a remote server (e.g., remote server 606) via a network (e.g., network 608) at 812. In some embodiments, the subsequent transmission may be made during an activity. For instance, some embodiments include a facility for a user to define certain time interval (e.g., 1 second, 5 seconds, 10 seconds, 1 minute, etc.) to make transmissions. In embodiments, the transmission may be made via Bluetooth, Bluetooth LE, or any suitable wireless technology and may be either via a server or directly with the remote device (e.g., smartphone, smart watch, or any capable mobile device).

Figure 9:
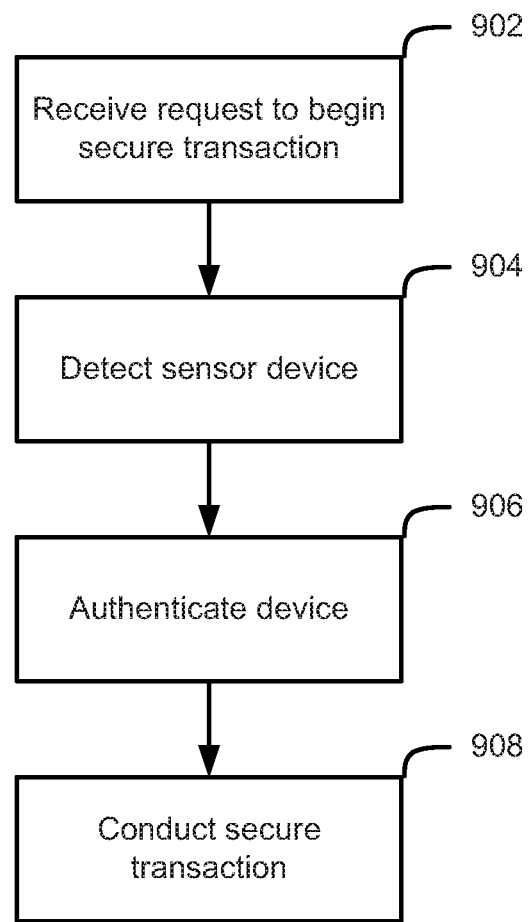
FIG. 9 is a flowchart illustrating a method of performing a secure transaction using a sensor device according to various embodiments.

In some embodiments, sensor device 112 may be used to facilitate secure transactions such as point of sale purchases using a wireless reader. An embodiment of this functionality if described with respect to FIG. 9. FIG. 9 will be described with respect to FIGS. 1A, 1B, 2, and FIGS. 6A and 6B. However, it should be understood that this is just for convenience and that the method depicted in FIG. 9 should not be construed as being limited to those specific embodiments.

FIG. 9 is a flowchart illustrating a method 900 for conducting a secure transaction using a sensor device (e.g., sensor device 112). As shown in FIG. 9, method 900 begins at 902 when a reader (e.g., payment reader 114) receives a request to initiate a secure transaction. For example, if the reader 114 is located near a point of sale device, the request may take the form of a user scanning an item or the like. After the request to begin the secure transaction is initiated, the reader 114 may detect the sensor device 112 at 904. According to various embodiments, the reader 114 may either actively or passively detect the sensor device 112, as discussed above with respect to FIG. 8. Additionally, the reader 114 may be configured to detect a sensor device 112 when it is physically in proximity to reader 114.

After detecting sensor device, the reader 114 may authenticate the sensor device at 906. According to embodiments, the authentication may take the form of the authentication discussed with respect to FIG. 6B. For example, in the case of a point of sale transaction, the sensor device 112 may provide to the reader 114 account information or unique ID information that can then be transmitted by the reader device 114 to a remote server (e.g., remote server 606). The remote server 606 can then perform authentication of the account information or unique ID (by, e.g., contacting a financial institution or third party) and transmit the result of the authentication to reader device 114. Upon authentication, the reader device 114 may be configured to conduct the secure transaction (e.g., authorize a sale, or the like) at 908.

In some embodiments in the case of a point of sale transaction, authentication of user account information and confirmation of a purchase of a new piece of athletic apparel (such as a pair of shoes) with an embedded sensor device 112 could automatically register the apparel with a user's online account. The user may then be prompted in the future to associate the apparel with particular activities, workout, training plans, events, etc.

Figure 10:
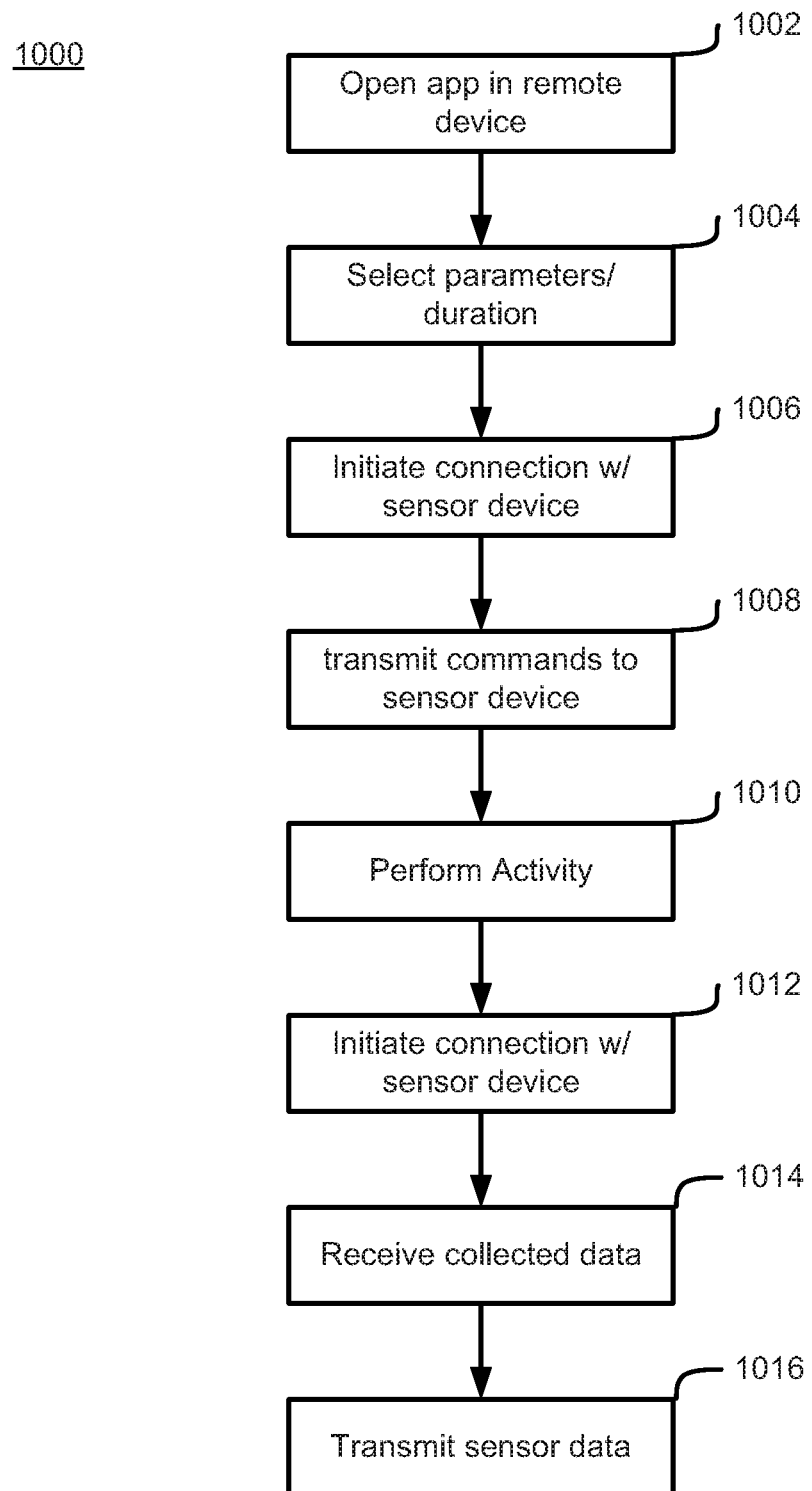
FIG. 10 is a flowchart illustrating a method of performing measurements using a sensor device according to various embodiments.

FIG. 10 is a flowchart illustrating how an individual 102 would use the sensor device and a remote device 104 to collect sensor data relating to an activity or exercise performed by the individual 102. FIG. 10 will be described with respect to FIGS. 1A, 1B, 2, and FIGS. 6A and 6B. However, it should be understood that this is just for convenience and that the method depicted in FIG. 10 should not be construed as being limited to those specific embodiments.

As shown in FIG. 10, the method 1000 can begin when a user opens an application specific to the sensor device 112 in the remote device 104 at 1002. For instance, if the remote device 104 is a smart phone, the a user may open an application (app) associated with the sensor device 112 embedded in apparel. In some embodiments, a specific app running on the remote device 104 may be configured to launch automatically based on detection of the sensor. For instance, if the sensor device 112 is a sensor for running, then a specific running app can be configured to launch based on detection of sensor device 112. Similarly, for example, the sensor device 112 is embedded in an outdoor shoe, then a specific outdoor app could be configured to be launched. Suitable apps may include, for example, those disclosed in commonly owned U.S. Pat. No. 9,392,941, which is incorporated herein by reference in its entirety. The app may then prompt a user to enter parameters and/or a duration of an activity or exercise at 1004. For instance, the user may be prompted to select which of several sensor items (e.g., speed, distance, heartbeat, temperature, etc.) that the user would like to be recorded by sensor device 112. In some embodiments, the user may be given several pre-selected groups of sensors to be used such that the pre-selected groups are tailored to a particular activity. Additionally, the user may be prompted to define a length of time that the sensor device 112 should perform its sensing function.

At 1006, a connection between the remote device 104 and the sensor device 112 may be initiated. In some embodiments, the connection may be initiated by placing the remote device 104 in close physical proximity to the sensor device 112 (e.g., "tapping" the remote device 104 to the sensor device 112). In one embodiment, the apparel housing the embedded sensor device 112 may include visual indicators such as stitching, embossing, printing, or functional items such as buttons or pockets that visually indicate to the wearer the location of the sensor device 112 which may otherwise not be visible to the user without the indicators. In some embodiments the indicators are specifically configured to signify the location of the sensor device 112 (like a crosshairs symbol), while in others (like buttons or pockets), the indicators have other functions or are traditional apparel accents and only additionally signal to the knowledgeable wearer the presence and location of the sensor device 112.

Once the connection between remote device 104 and sensor device 112 has been initiated at 1006, the remote device 104 may transmit necessary commands to sensor device 112. For instance, the remote device 104 may transmit commands that indicate which of a number of sensors should be activated and what information from those sensors should be stored in the memory 206 of the sensor device 112. Additionally, the remote device 104 may instruct the sensor device 112 regarding a duration of sensor activity.

At 1010, the user may perform the activity or exercise that the sensor device will record and, after the user completes the activity or exercise, a subsequent connection between the remote device 104 and the sensor device 112 may be initiated at 1012. After initiating the subsequent connection, the collected data can be received from the sensor device 112 at 1014. The remote device 104 may then optionally transmit the received sensor data or data based on the received sensor data to a remote server (e.g., server 606) at 1016 for, e.g., later access by the user.

Suitable portable fitness or activity monitoring software applications may include, for example, the features of those disclosed in commonly owned U.S. Pat. No. 9,392,941, which is incorporated herein by reference in its entirety.

In some embodiments, the software app running on the remote device 104 may also include "hidden" features that cannot be accessed unless unlocked in standard operation of the app without an additional step. In one embodiment, the additional step may include the selection or purchase of a particular health or fitness goal or workout plan, attaining particular personal performance metrics, or activating the app during a specified time period (e.g. on a holiday or particular day of the week) or when the remote device 104 is being used in a specified geographical location (e.g. in a specific city, park, etc.).

In some embodiments, the status (i.e., whether they are locked or unlocked) of the "hidden" features may be stored in memory of the remote device 104. For instance, in some embodiments, the "hidden" features by be activated by a communication from one or more sensor devices 112. By way of example, consider a case where sensor device 112 is embedded in a pair of shoes, as is shown in FIG. 1A with respect to sensor device 106. It may be possible to have hidden features (e.g., the calculation or display of metrics that are relevant to runners) remain locked in the software app until they are specifically unlocked by communication between the remote device 104 and the sensor device 112. Once unlocked, the software app may be enabled to perform the specialized calculations or provide specialized feedback and subsequently make it available to the individual 102 via mobile device 118.

In another embodiment, when the remote device 104 is placed in close physical proximity to the sensor device 112 embedded in the article of apparel (e.g., "tapping" the remote device 104 to the sensor device 112), the remote device 104 may be configured to open an app, and to use the registration information from the app to also register the article of apparel associated with the sensor device 112.

In all embodiments, the application cache may take the form of a bytecode cache, a source code cache, a machine code cache, or some combination thereof. In an embodiment, the predictive cache contains two or more levels of cache. For example, one embodiment includes both a source code cache and a bytecode cache. Translating or compiling source code to byte code takes processing time and resources, therefore the predictive cache should only compile and store bytecode for applications that have a higher likelihood of being launched. Therefore, in an embodiment, the bytecode cache is reserved for the higher priority applications and the source code cache is reserved for lower priority applications. One example of this type of distinction would be to cache bytecode for applications with a predictive score above a certain threshold, and only cache source code for applications with a predictive score below that threshold.

Figure 11:
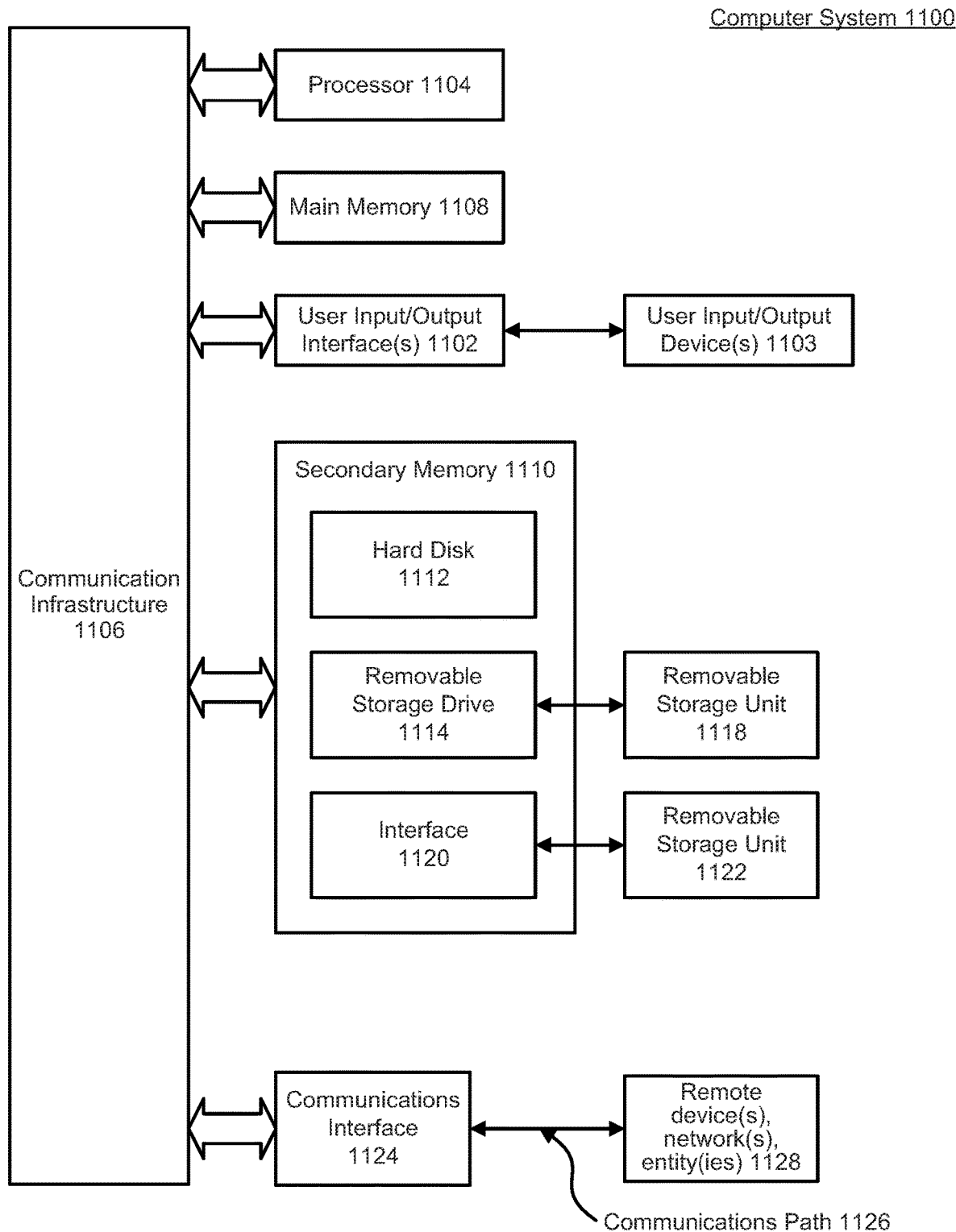
FIG. 11 is an example computer system useful for implementing various embodiments.

Embodiments shown in FIG. 1-10 can be implemented, for example, using one or more well-known computer systems or one or more components included in computer system 1100 shown in FIG. 11. Computer system 1100 can be any well-known computer capable of performing the functions described herein.

Computer system 1100 includes one or more processors (also called central processing units, or CPUs), such as a processor 1104. Processor 1104 is connected to a communication infrastructure or bus 1106.

One or more processors 1104 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1100 also includes user input/output device(s) 1103, such as monitors, keyboards, pointing devices, etc., that communicate with communication infrastructure 1106 through user input/output interface(s) 1102.

Computer system 1100 also includes a main or primary memory 1108, such as random access memory (RAM). Main memory 1108 may include one or more levels of cache. Main memory 1108 has stored therein control logic (i.e., computer software) and/or data.

Computer system 1100 may also include one or more secondary storage devices or memory 1110. Secondary memory 1110 may include, for example, a hard disk drive 1112 and/or a removable storage device or drive 1114. Removable storage drive 1114 may be a floppy disk drive, a magnetic tape drive, a compact disk drive, an optical storage device, tape backup device, and/or any other storage device/drive.

Removable storage drive 1114 may interact with a removable storage unit 1118. Removable storage unit 1118 includes a computer usable or readable storage device having stored thereon computer software (control logic) and/or data. Removable storage unit 1118 may be a floppy disk, magnetic tape, compact disk, DVD, SD-Card, optical storage disk, and/or any other computer data storage device. Removable storage drive 1114 reads from and/or writes to removable storage unit 1118 in a well-known manner.

According to an exemplary embodiment, secondary memory 1110 may include other means, instrumentalities or other approaches for allowing computer programs and/or other instructions and/or data to be accessed by computer system 1100. Such means, instrumentalities or other approaches may include, for example, a removable storage unit 1122 and an interface 1120. Examples of the removable storage unit 1122 and the interface 1120 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1100 may further include a communication or network interface 1124. Communication interface 1124 enables computer system 1100 to communicate and interact with any combination of remote devices, remote networks, remote entities, etc. (individually and collectively referenced by reference number 1128). For example, communication interface 1124 may allow computer system 1100 to communicate with remote devices 1128 over communications path 1126, which may be wired and/or wireless, and which may include any combination of LANs, WANs, the Internet, etc. Control logic and/or data may be transmitted to and from computer system 1100 via communication path 1126.

In an embodiment, a tangible apparatus or article of manufacture comprising a tangible computer useable or readable medium having control logic (software) stored thereon is also referred to herein as a computer program product or program storage device. This includes, but is not limited to, computer system 1100, main memory 1108, secondary memory 1110, and removable storage units 1118 and 1122, as well as tangible articles of manufacture embodying any combination of the foregoing. Such control logic, when executed by one or more data processing devices (such as computer system 1100), causes such data processing devices to operate as described herein.

What is claimed is:

1. An electronic device embedded in an article of apparel for monitoring an individual engaged in a physical activity, the electronic device comprising:
   a sensor device configured to detect data relating to the physical activity;
   a memory configured to store the detected data and to store payment data associated with the individual;
   a wireless interface configured to communicate with a first external communication device and a second external communication device; and
   one or more processors communicatively coupled to the wireless interface, the one or more processors configured to:
      receive a command from the first external communication device;
      cause the sensor device to detect the data in response to the receiving of the command;
      receive a transaction request from the second external communication device; and
      cause the wireless interface to transmit the payment data to the second external communication device in response to the receiving of the transaction request.

2. The electronic device of claim 1, wherein the one or more processors are further configured to:
   receive a request for authentication data from the second external communication device; and
   cause the wireless interface to transmit the authentication data to the second external communication device in response to the receiving of the request.

3. The electronic device of claim 2, wherein the authentication data comprises information configured to be used by the second external communication device to authenticate the sensor device.

4. The electronic device of claim 2, wherein the authentication data comprises personal identification information of the individual.

5. The electronic device of claim 1, wherein the payment data comprises a financial account number.

6. The electronic device of claim 1, wherein the payment data comprises an identification of a financial institution.

7. The electronic device of claim 1, wherein the payment data comprises an apparel account identifier.

8. A method for carrying out a financial transaction using an electronic device embedded in an article of apparel for monitoring an individual engaged in a physical activity, the method comprising:
- receiving a command from a first external communication device, wherein the command indicates data to be collected and stored in a memory;
- detecting the data indicated in the command, wherein the data relates to the physical activity;
- storing the detected data and payment data associated with the individual in the memory;
- receiving a transaction request from a second external communication device; and
- transmitting the payment data to the second external communication device in response to the receiving of the transaction request.

9. The method of claim 8, further comprising:
- receiving a request for authentication data from the second external communication device; and
- transmitting the authentication data to the second external communication device in response to the receiving of the request.

10. The method of claim 9, wherein the authentication data comprises information configured to be used by the second external communication device to authenticate a sensor device.

11. The method of claim 9, wherein the authentication data comprises personal identification information of the individual.

12. The method of claim 8, wherein the payment data comprises a financial account number.

13. The method of claim 8, wherein the payment data comprises an identification of a financial institution.

14. The method of claim 8, wherein the payment data comprises an apparel account identifier.

15. A method for carrying out a financial transaction of an article of apparel for monitoring an individual engaged in a physical activity, comprising:
- detecting a sensor device embedded within the article of apparel;
- transmitting a command and a transaction request to the sensor device, wherein the command indicates sensor data to be stored by the sensor device and the transaction request is configured to initiate a transaction with the article of apparel;
- receiving the sensor data from the sensor device;
- receiving payment information from the sensor device in response to receiving the transaction request;
- communicating with a financial institution associated with the payment information; and
- receiving payment confirmation from the financial institution.

16. The method of claim 15, further comprising:
- transmitting a request for authentication data to the sensor device; and
- receiving authentication data in response to the request.

17. The method of claim 16, wherein the authentication data comprises identification information of the individual.

18. The method of claim 16, wherein the authentication data comprises account information.

19. The method of claim 18, further comprising:
- automatically registering the article of apparel with a user account identified by the account information.

20. The method of claim 19, further comprising receiving confirmation from an apparel company that the article of apparel has been registered to an apparel account of the individual.

* * * * *